Figure 1:
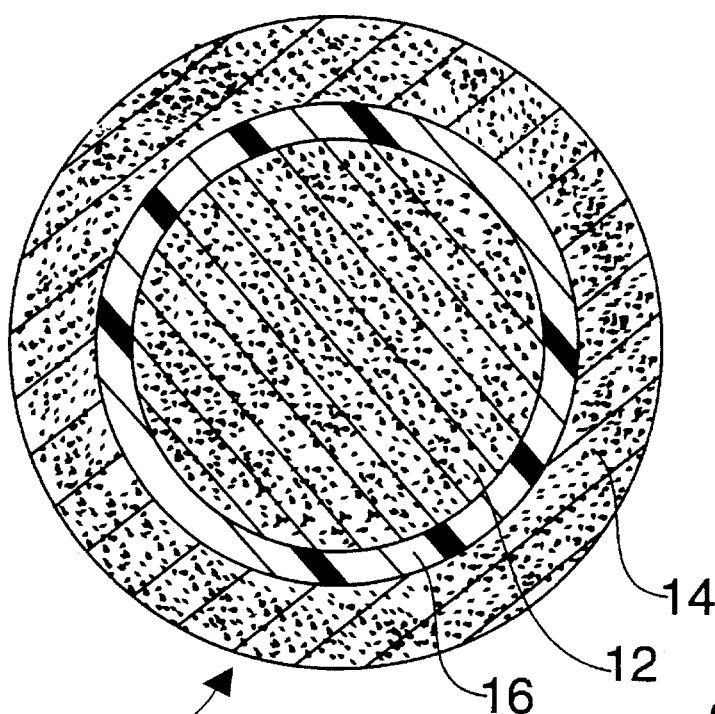

United States Patent [19] [11] Patent Number: 5,526,607
Roesch et al. [45] Date of Patent: *Jun. 18, 1996

[54] WATER DISPERSIBLE DELIVERY SYSTEM FOR AN AGRICULTURALLY ACTIVE CHEMICAL

[75] Inventors: Susan M. Roesch; Leonard J. Goldman; Charles L. Beatty, all of Gainesville, Fla.

[73] Assignee: Net/Tech International, Baldwin, N.Y.

[*] Notice: The term of this patent shall not extend beyond the expiration date of Pat. No. 5,335,449.

[21] Appl. No.: 143,467

[22] Filed: Oct. 26, 1993

Related U.S. Application Data

[63] Continuation-in-part of Ser. No. 745,635, Aug. 15, 1991, Pat. No. 5,335,449, and a continuation-in-part of Ser. No. 978,219, Nov. 18, 1992, Pat. No. 5,346,541.

[51] Int. Cl.$^6$ ..................................................... A01G 9/02
[52] U.S. Cl. ................................................. 47/66; 47/48.5
[58] Field of Search ........................................ 47/48.5, 66

[56] References Cited

U.S. PATENT DOCUMENTS

| | | |
|---|---|---|
| 2,222,815 | 11/1940 | Johnson . |
| 2,543,580 | 2/1951 | Kay . |
| 2,771,377 | 11/1956 | Greminger et al. . |
| 2,858,647 | 11/1958 | Cotton . |
| 2,965,508 | 12/1960 | Windover et al. . |
| 3,003,911 | 10/1961 | Lindstrom et al. . |
| 3,376,285 | 4/1968 | Callihan et al. . |
| 3,455,714 | 7/1969 | Bishop et al. . |
| 4,031,179 | 6/1977 | Tatzel et al. . |
| 4,508,595 | 4/1985 | Gasland . |
| 4,698,264 | 10/1987 | Steinke . |
| 4,744,976 | 5/1988 | Snipes et al. . |
| 4,765,982 | 8/1988 | Ronning et al. . |
| 4,780,317 | 10/1988 | Sekikawa et al. . |
| 4,806,337 | 2/1989 | Snipes et al. . |
| 4,851,227 | 7/1989 | Markus et al. . |
| 4,888,145 | 12/1989 | Allner et al. . |
| 4,889,719 | 12/1989 | Ohtsubo et al. . |
| 4,891,223 | 1/1990 | Ambegaonkar et al. . |
| 5,025,004 | 6/1991 | Wu et al. . |
| 5,039,524 | 8/1991 | Oishi et al. . |
| 5,110,525 | 5/1992 | Kolsky et al. . |
| 5,189,152 | 2/1993 | Hinterholzer et al. . |

FOREIGN PATENT DOCUMENTS

| | | |
|---|---|---|
| 1103389 | 2/1968 | United Kingdom . |
| 1269622 | 4/1972 | United Kingdom . |
| 1371179 | 10/1974 | United Kingdom . |
| 1371096 | 10/1974 | United Kingdom . |
| 2027346 | 2/1980 | United Kingdom . |
| 20525443 | 3/1983 | United Kingdom . |
| 9117210 | 11/1991 | WIPO . |

*Primary Examiner*—Randolph A. Reese
*Assistant Examiner*—Joanne C. Downs
*Attorney, Agent, or Firm*—Henry D. Coleman; R. Neil Sudol

[57] ABSTRACT

A delivery system for a biocide or fertilizer comprises a body or carrier portion including a first water dispersible agriculturally inert and essentially nontoxic composition containing a predetermined amount of the biocide or fertilizer. The body or carrier portion has a predetermined size and shape. The delivery system also comprises a protective coating, about the body portion, of a second water dispersible agriculturally inert and essentially nontoxic composition. The amount of biocide used is that amount which terminates the functioning of a target agricultural pest upon application of the biocide to soil or water via the delivery system. The biocide can take the form of a biocide such as an insecticide, fungicide, nematocide or herbicide. Compositions according to the present invention including a water dispersible cellulose ether, cellulose fiber and an effective amount of a biocide or fertilizer are also described. Additional components may be added to the composition according to the present invention.

21 Claims, 2 Drawing Sheets

WATER DISPERSIBLE DELIVERY SYSTEM FOR AN AGRICULTURALLY ACTIVE CHEMICAL

RELATED APPLICATIONS

This application is a continuation-in-part of patent application Ser. No. 745,635, filed Aug. 15, 1991, entitled "Delivery System for an Agriculturally Active Chemical", now U.S. Pat. No. 5,335,449, and a continuation-in-part of patent application Ser. No. 978,219, filed Nov. 18, 1992, entitled "Water Dispersible Formulations and Materials and Methods for Influencing Their Water Dispersibility," now U.S. Pat. No. 5,346,541.

BACKGROUND OF THE INVENTION

This invention relates to a delivery system for a biocide such as an insecticide, fungicide, nematocide, herbicide or other pesticide. This invention also relates to a method of making such a delivery system. This invention also relates to water dispersible compositions containing an effective amount of a biocide or fertilizer.

The dangers of using biocides such as insecticides, fungicides, nematocides or other pesticides are largely known. Generally, such substances pose significant, if not substantial, threat to human beings who come into contact with the chemicals during manufacturing or application of the chemical to a target to be treated, for example, agricultural crops. Great care must be taken in tapping the transport drums and in mixing the chemicals with water prior to a spraying or other distribution operation. Protecting workers from the dangers of the chemicals gives rise to delays and concomitantly increased expense of agricultural production.

Although on a reduced scale, similar dangers exist in the home-use market. Chemicals for the home market are also shipped in liquid form, in smaller containers. The chemicals must be mixed with water and otherwise handled, which increases the risk of harm to the user and even to innocents such as children.

OBJECTS OF THE INVENTION

An object of the present invention is to provide an essentially non-toxic delivery system for an agriculturally active chemical, especially a biocide.

A more particular object of the present invention is to provide such a delivery system wherein human contact with the biocide is reduced, if not eliminated.

Another particular object of the present invention is to provide such a delivery system which is utilizable in home use applications, as well as in large-scale agricultural applications.

An additional object of the present invention is to provide a delivery system for a delayed release of a biocide.

A further particular object of the present invention is to provide a delivery system which is essentially agriculturally inert, except for the biocide to be delivered or applied.

Yet another object of the present invention is to provide a method for making a delivery system for an agriculturally active chemical.

Still a further object of the present invention is to provide such a method wherein the delivery system can be made in different shapes.

Still another object of the present invention is to provide methods for enhancing or reducing the rate of water dispersibility of formulations according to the present invention which include an biocide.

Yet an additional object of the present invention is to provide water dispersible compositions for use in delivering a biocide.

These and other objects according to the present invention may be readily gleaned from a description of the invention which follows.

SUMMARY OF THE INVENTION

A delivery system for a biocide such as an insecticide, a nematocide, a herbicide or other pesticide, comprises, in accordance with the present invention, a body portion including a first water dispersible agriculturally inert and essentially nontoxic composition which comprises a water dispersible cellulose ether in combination with cellulose fibers, and optionally, a predetermined amount of a biocide preferably dispersed throughout the first water dispersible composition and other components such as fillers, binders and gas releasing agents, among others.

The body portion of the delivery system preferably has a predetermined size and a predetermined shape. The delivery system may also preferably comprise a protective coating, about the body portion, or a cap or lid of a second water dispersible agriculturally inert and essentially nontoxic composition. The first and second water dispersible agriculturally inert compositions may be the same composition or a different composition. The second water dispersible composition also comprises a water dispersible cellulose ether binder material in combination with cellulose fibers and optionally, other components such as fillers, binders and gas releasing agents, among others. Both the first and second water dispersible compositions may include effective amounts of either the same or different biocide(s).

In certain preferred embodiments a cup-shaped body portion is used, with biocide being placed alone or in combination with a filler, dispersing agent or other additive within the cup-shaped body portion. In this aspect according to the present invention, the biocide with additive is placed within the cup-shaped body portion and is capped or enclosed with a lid. In this aspect according to the present invention, the body portion and the cap or lid encloses the biocide and additive. The body portion and lid are both made of a water dispersible composition comprising a water dispersible cellulose ether binder material in combination with cellulose fibers and optionally, other components such as fillers, binders and gas releasing agents, among others. Preferably, the body portion and the cap or lid are made of the same material.

The amount of the biocide is that amount effective to substantially terminate the biological functioning of a significant number of target agricultural pests upon application of the biocide to soil or other substrate via the delivery system.

The body portion preferably takes the shape of a pellet for certain home use and large-scale agricultural applications. Because the pellets are preferably provided with a protective coating of a nontoxic composition (containing no biocide), no special or extraordinary precautions need be taken for the transport and handling of the pellets. Shipping containers may be recycled or disposed of in any ecologically suitable manner. Generally, in preferred embodiments, the pellets themselves may be handled by hand without danger of contamination by the biocide.

A number of pellets for delivering biocide to a substrate is selected by the user in accordance with the size of the application. For example, doubling the area to be protected generally requires twice the number of pellets. The selected pellets are simply placed into a container of water and allowed to disperse. Upon dispersion of the pellets, the biocide dissolves or disperses in the water. The residue from the agriculturally inert and essentially nontoxic compositions is partially dissolved, partially suspended in solution and may precipitate out to a minor extent. The residue, however, is preferably completely dispersible in water. In certain preferred embodiments, the composition does not clog spraying or other application equipment.

The term "biocide" is used throughout the specification to describe a biologically active chemical which has use in agriculture. Such compounds may include biocides, but may also include chemicals which modify the growth of plants. These compounds may be natural or synthetic chemicals and may include biochemicals such as genetically engineerd products.

The term "fertilizer" is used throughout the specification to describe a chemical composition which promotes the growth of plants. The term includes both natural and synthetic chemicals, including genetically engineered products. Compositions according to the present invention may include biocides and/or fertilizers.

The term "cellulose" is used throughout the specification to describe any composition having the formula $(C_6H_{10}O_5)_n$, where n is an integer greater than 5.

The term "cellulose fiber" is used throughout the specification to describe fibers made of cellulose which are added to the water dispersible cellulose ether binder to provide strength and integrity to the material and to influence the rate of water dispersibility of the materials. Cellulose fibers according to the present invention may be long, short or mixtures of long and short fibers. The length of the cellulose fiber may dramatically influence the water dispersibility rates of compositions according to the present invention. Cellulose fibers may be derived from a number of sources including tissue paper, wood pulp as well as other sources.

The term "short cellulose fiber" or "short fiber" is used throughout the specification to describe cellulose fibers which are less than about 300 microns in length and most preferably range from about 22 microns to about 280 microns in length. Short cellulose fibers useful in the present invention may be processed from one or a mixture of plant, preferably, tree species. Short cellulose fibers may be included in compositions according to the present invention to influence dispersibility times. In the present invention, preferred short cellulose fibers for use in the present invention include those obtained from Fiber Sales and Development Corporation, Urbana, Ohio under the tradename Solka-Floc.

The term "long cellulose fiber" or "long fiber" is used throughout the specification to describe cellulose fibers which are greater than about 300 microns in length and most preferably range from about 300 microns to 2 mm or more in length. Exemplary long cellulose fiber for use in the present invention are derived primarily from wood pulp (although other types of fiber derived from other plant material may also be used). Examples of such wood pulp include wood pulp derived from soft and hard wood, for example, Leaf River 90 Softwood (Leaf River, Ala.), Brunswick Prime Softwood (Brunswick, Ga.), Ashdown Prime Softwood (Ashdown Ark.), Brunswick E-100 (Brunswick, Ga.), Puget Fluff and Puget Ultra, (Bellingham, Wash.), Ashwood Prime Hardwood (Ashdown, Ala.), Palatka Prime Hardwood (Woodland, Me.) and Woodland St. Croix Hardwood (Woodland, Me.). Suppliers of cellulose fibers for use in the present invention include Georgia-Pacific Corporation, Atlanta, Ga., James River Corporation, Richmond Va., Westvaco of Wickliffe, Ky., Weyerhauser Corp., Tacoma, Wash., Great Northern Nekoosa of Atlanta, Ga. and Potlatch Corporation, San Francisco, Calif. Chemically debonded pulps may also be used in the present invention.

The term "water dispersible cellulose ether" is used throughout the specification to describe water soluble or water dispersible cellulose ether materials which can be used as binders in the present invention. Water soluble cellulose ethers for use in the present invention include, for example, carboxymethylcellulose (CMC), hydroxypropylcellulose (HPC), hydroxypropylmethylcellulose (HPM), hydroxyethylcellulose (HEC), methylcellulose (MC), hydroxymethylethylcellulose (HMEC) and carboxylmethylhydroxyethylcellulose (CMHEC) and any related cellulose ether derivative which is readily soluble or dispersible in water. These binder materials are readily available from a number of chemical distributors including Aqualon, Dow Chemical Co. and Union Carbide under such tradenames as carboxymethylcellulose "7LXF" and hydroxypropylcellulose "Klucel Type GF", hydroxypropylmethylcellulose "Methocel F50" and hydroxyethylcellulose "Cellosize QP 4400-H". The cellulose ether binders which are used in the present invention may vary over a wide molecular weight range, but preferably range in molecular weight from about 100,000 to about 500,000. Above a molecular weight of 500,000, the cellulose ether binders produce solutions/dispersions of high viscosity having low water dispersibility.

The term "gas-producing agent" or "gas-releasing agent" is used throughout the specification to describe an agent which, when added to a water dispersible cellulose ether, releases a gas such as oxygen, carbon dioxide, nitrogen, ammonia and hydrogen, among other gases. While not being limited by way of theory, it is believed that the result of the addition of effective amounts of a gas-releasing agent to formulations according to the present invention is to release gas and produce a "foaming action." This foaming action, in turn, produce pores throughout the interstices of the cellulose ether binder matrix. The result is a formulation with substantially enhanced water dispersibility and surprising strength and structural integrity. Gas releasing agents for use in the present invention include, for example, peroxides (which release oxygen), especially hydrogen peroxide, hydrides (which release hydrogen), azo compounds such as azoisobutyronitrile (AIBN) which release nitrogen at elevated temperatures, urea and urea-like agents which release ammonia gas, bicarbonates such as sodium and potassium bicarbonate, among others, and carbonates such as ethylene carbonate, propylene carbonate and sodium and potassium carbonate which will release substantial quantities of carbon dioxide alone (at elevated temperature) or when exposed to an acid. Preferred gas releasing agents for use in the present invention include peroxides, especially including hydrogen peroxide and a salt of bicarbonate such as sodium or potassium bicarbonate in combination with a biodegradable, biologically compatible organic acid such as citric acid, among others.

The term "effective amount" is used throughout the specification to describe that amount of a component added to the formulations according to the present invention to produce an intended result or to provide a certain characteristic to formulations according to the present invention.

In certain applications according to the delivery system aspect of the present invention, the body portion of the delivery system may take the form of a container, for example, a pot or other cup-shaped receptacle, into which a seedling may be placed. The receptacle with its contents is then placed in the soil and eventually disperses with rain and watering, so that the biocide is gradually applied in the soil about the seedling.

The biocide is preferably an insecticide, fungicide, nematocide or herbicide. More particularly, the biocide is a compound selected from the group consisting of dimethoate, vydate, vendex, metasystox-R, fluvalinate and kethane, invermectin, propoxur, chlorpyrifos, diazinon, malathion, carbaryl, fenvalerate, methomyl, acephate, permethrins, diflubenzuron and mixtures thereof.

Dimethoate (CYGON), vydate, vendex, metasystox-R, fluvalinate (MAVRIK) and kethane are particularly suitable for placement into the soil in a shipment container. If the soil is kept moist for shipping, the pesticide would be released slowly and continously from the water-dispersible material during shipment and the plants in the containers would be insect free upon arrival at their destinations.

Invermectin is suitable for use as a nematocide. The water dispersible substrate carries the nematocide into soil near the roots of a plant. Watering will then allow direct interaction of the nematocide with nematodes.

Propoxur (BAYGON), chlorpyrifos (DURSBAN), diazinon, malathion, carbaryl (SEVIN) are considered suitable for home-use applications. For both indoor and outdoor spraying, a predetermined number of pellets is dissolved in water and eliminates many hazards and inconveniences associated with home spraying.

Chlorpyrifos (LORSBAN), fenvalerate (PYDRIN), methomyl (LANNATE, NUDRIN), acephate (ORTHENE), permethrins (AMBUSH, POUNCE), and diflubenzuron (DIMILIN) are useful in pre-packaged biologically degradable carriers as described herein, particularly for small farmers to conform to many new regulations on pesticides.

Pursuant to a particular embodiment of the present invention, the biocide may be interspersed throughout the first water dispersible agriculturally inert and essentially nontoxic composition. This embodiment is especially advantageous for applications calling for a gradual release of the biocide over a period of time. After the protective coating is dispersed, the body portion of the delivery system gradually disperses and releases the biocide.

Pursuant to an alternative embodiment of the present invention, the body portion is hollow and defines a chamber, the biocide being disposed at least partially within the chamber. The biocide may be included in the chamber alone or preferably, with any number of diluents and additives to facilitate dissolution or dispersion of the biocide in water.

Pursuant to another feature of the present invention, at least one of the water dispersible agriculturally inert and essentially nontoxic compositions includes a water dispersible cellulose ether and a cellulose fiber. Optionally, a number of other components may also be included, for example, stearic acid or any one of its related salt compositions as well as other fillers and binders, and gas releasing agents as described above. The related stearic salt compositions generally include potassium stearate, sodium stearate and zinc stearate.

The cellulose fiber preferably comprises about 10% to 90%, more preferably about 20% to 75% by weight of the water dispersible agriculturally inert and essentially nontoxic composition. The cellulose ether binder preferably comprises between approximately 2% and 75%, more preferably about 10% to about 65% by weight of the water dispersible agriculturally inert and essentially nontoxic composition.

The compositions according to the present invention may also include a gas releasing agent such as peroxides, salts of biocarbonate and carbonate, among others as described hereinabove. The compositions according to the present invention preferably include about 0.01% to about 30% and more preferably about 0.1% to about 15% by weight of a gas releasing agent. It is to be noted that the amount and type of gas releasing agent used in the compositions according to the present invention may have a dramatic impact on the water dispersiblity of the compositions according to the present invention. It is noted that the effect on dispersal rate is a function of the type of gas releasing agent used. It is further noted that depending upon the amount and type of gas releasing agent used, dispersal times may actually increase dramatically relative to the use of water soluble cellulose ether binders alone.

In addition, stearic acid or a salt of stearate may also be included as a filler. Such fillers preferably comprise between 0% and about 25%, more preferably about 4% to about 25% by weight of the water dispersible agriculturally inert and essentially nontoxic composition.

The cellulose fiber may take the form of shredded tissue paper, unbleached cellulose fiber from wood pulp, and cellulose fibers derived from numerous plants and from hard or soft wood pulp, among numerous others. Any type of cellulose fiber will have utility in the instant invention. Additional components such as diluents, dispersants, surfactants and other additives may be included within the nontoxic compositions for use in the present invention.

It has been unexpectedly discovered that the inclusion of at least about 10% by weight cellulosic fibers derived from wood pulp dispersed randomly throughout a water dispersible cellulose ether matrix provides for a water dispersible composition which has surprising strength and great structural integrity without the need for adding other structural fillers used in the prior art, for example, glass wool and related glass fibers.

In embodiments in which the biocide agent is released from the water dispersible nontoxic composition, it is recognized that the composition may be varied within the teachings of the present invention to vary the rate of release of the biocide agent. This may be done by changing the type and amount of the cellulose ether binder utilized, the type and amount of cellulose fibers utilized, the type and amount of binder utilized as well as including gas releasing agents and other agents which have been shown to influence the rate at which the composition disperses in water.

In certain preferred aspects according to the present invention, an effective amount of at least one gas releasing agent is preferably added to the cellulosic fibers and water dispersible cellulose ether binder matrix. Such compositions may also include optional additives such as inert fillers, including calcium carbonate, talc, stearic acid salts such as zinc stearate, among others or clay powder and $TiO_2$, plastizers, insolubilizers or cross-linking agents, surface and dispersal agents, fragrances, compounds to attract agricultural pests to the included pesticide and coloring agents.

It is to be noted that the cellulose fibers for inclusion in the water dispersible composition may be sized to influence the water dispersibility of the composition. Thus, by including cellulose fibers of varying sizes within the matrix comprising the water dispersible cellulose ether material, the water dispersibility of the composition may be varied widely. The advantage to this aspect of the present invention is that numerous water dispersible materials can be manufactured suited to a wide variety of purposes based upon the varying dispersibility rates.

While the weight of cellulose fibers, water dispersible cellulose ether and other additives serve as useful guides to produce water dispersible compositions according to the present invention, one of ordinary skill in the art will recognize that the amount of each of the components added to formulations according to the present invention may be varied outside of these ratios when other additives are included. Cellulose fibers for use in the present invention preferably include products which are derived from plants and/or wood pulp. These products are processed for use according to fiber size and are available from a number of well known suppliers.

In certain aspects according to the present invention the water dispersible compositions may further include calcium carbonate and/or polyvinylalcohol. When included, the calcium carbonate preferably comprises between approximately 0% and 10% of the respective water dispersible composition. The polyvinylalcohol, when included, preferably comprises between approximately 0% and 15% of the respective water dispersible agriculturally inert and essentially nontoxic composition.

Pursuant to another feature of the present invention, the compositions according to the present invention may further include a surfactant. Useful surfactants include a wide variety of ionic, non-ionic and amphoteric surfactants readily available in the art.

Compositions according to the present invention may be utilized in the biocide delivery system aspect of the present invention as the first and/or second water dispersible agriculturally inert and essentially nontoxic composition.

According to a further embodiment of the present invention, a layer of a water soluble polymer may be included in the water dispersible agriculturally inert and essentially nontoxic composition or alternatively, disposed between the body portion and the coating. The polymer interlayer, when disposed between the body portion and the coating, functions to prevent or inhibit diffusion of the biocide from the inner body portion of the delivery system into the protective coating. The polymer interlayer preferably comprises one or more of the following: acrylics, polyvinylidene chloride, ionomer, polyvinylalcohol, and polyethylhydroxycellulose.

A method for making a delivery system for a biocide comprises, in accordance with the present invention, the step of forming a body portion including a first water dispersible agriculturally inert and essentially nontoxic composition which contains a predetermined aliquot of the biocide. The body portion has a predetermined size and a predetermined shape. In another step, a protective coating of a second water dispersible agriculturally inert and essentially nontoxic composition is placed about the body portion. The aliquot of the biocide is an amount effective to substantially terminate the functioning of a significant number of target agricultural pests upon application of the biocide to the area to be treated (e.g., soil, crops, a body of water) via the delivery system.

In accordance with another feature of the present invention, the step of forming the body portion includes the steps of (a) providing a first dough including water, the first water dispersible agriculturally inert and essentially nontoxic composition and a predetermined amount of the biocide, (b) forming the dough into the body portion, and (c) drying the body portion while the dough is maintained in the predetermined shape. Pursuant to this manner of forming the body portion of the delivery system, the biocide is combined with the ingredients of the first dough prior to the shaping and drying of the dough. The dough may be molded, sculpted, extruded, pressed or otherwise shaped to form any of a variety of different shapes. A pellet and a pot or cup shape are two preferred forms for the delivery system.

In accordance with another feature of the present invention, the step of placing the protective coating about the chemical-bearing body portion comprises the steps of (i) providing a second dough including water and the second water dispersible agriculturally inert and essentially nontoxic composition, (ii) applying the second dough in a layer about the dried body portion, and (iii) drying the layer of the second dough about the body portion.

The application of the second dough to the dried core or chemical-bearing body portion may be implemented by any suitable technique. For example, the dried body portion may be dipped into a vat of the second dough and then removed from the vat with a layer of the second dough. The second dough may also be molded or pressed about the dried shapes of the body portions.

In accordance with an alternative feature of the present invention, the step of forming the body portion includes the steps of (a) providing a first dough including water and the first water dispersible agriculturally inert and essentially nontoxic composition, (b) shaping the first dough into a container preform, (c) drying the preform, (d) providing the aliquot of the biocide, and (e) depositing the aliquot into the dried preform.

The aliquot of the biocide may be injected, sprayed, dropped or otherwise deposited into the container-like preform. The protective coating on the preform may be placed about the core or body portion as set forth above. A second dough including water and the second water dispersible agriculturally inert and essentially nontoxic composition is provided and applied in a layer about the dried body portion. The layer of the second dough about the body portion is then dried.

Pursuant to another feature of the present invention, a layer of a water soluble or water dispersible polymer is applied between the body portion and the protective coating. The polymer preferably comprises one or more of the following: acrylics, polyvinylidene chloride, an ionomer, polyvinylalcohol, and polyethylhydroxycellulose and may be applied by spraying, rolling, dipping, or brushing.

An alternative method in accordance with the present invention for making a delivery system for an biocide comprising the steps of providing a first dough including water and a first water dispersible agriculturally inert and essentially nontoxic composition, extruding the dough to form a tube, and drying the tube. A second dough including water, a second water dispersible agriculturally inert and essentially nontoxic composition and a predetermined amount of the biocide is then formed as a core inside the dried tube. The core is dried and the tube with the core is then cut to form a plurality of segments. The ends of the segments are capped with dough including water and a third water dispersible agriculturally inert and essentially nontoxic composition. Subsequently, the capped ends of the segments are dried.

Yet another method for making a delivery system for a biocide comprises, in accordance with the present invention, the steps of providing a first dough including water and a first water dispersible agriculturally inert and essentially nontoxic composition, extruding the dough to form a tube, drying the tube and cutting the tube to form a plurality of tubular segments. A second dough including water, a second water dispersible agriculturally inert and essentially nontoxic composition and a predetermined amount of the biocide is provided and formed as a core inside each of the segments. The core inside each of the segments is then dried, the ends of the segments are capped with dough including water and a third water dispersible agriculturally inert and essentially nontoxic composition, and the capped ends are dried.

A delivery system in accordance with the present invention is substantially non-toxic. Pursuant to the present invention, biocides can be applied to a garden or crop without human beings coming into significant contact with the chemicals.

In certain embodiments, a delivery system in accordance with the present invention provides for a delayed release of the biocides. The chemicals may be released by the gradual dispersion of water-dispersible carrier materials, namely, the agriculturally inert and essentially nontoxic compositions. In the dried state of the formed carrier bodies, the compositions in accordance with the present invention are tough and flexible and can be formed, e.g., molded, pressed, sculpted or otherwise manipulated, into a variety of different shapes.

It is to be noted that a delivery system in accordance with the present invention involves basically a biodegradable carrier and can be used to apply a biodegradable pesticide. The biocide pesticide, whether a herbicide, fungicide, insecticide or nematocide, may itself be biodegradable or genetically engineered. The biocide or pesticide disperses upon dispersion of the carrier and diffuses into the soil or water.

BRIEF DESCRIPTION OF THE DRAWING

FIG. 1 is a cross-sectional view of a pellet, in accordance with the present invention, for use in delivering an biocide.

FIG. 2 is a cross-sectional view of another pellet, in accordance with the present invention, for use in delivering an biocide.

FIG. 3 is a cross-sectional view of a cup-shaped device, in accordance with the present invention, for use in delivering an biocide.

FIG. 4 is a diagram illustrating successive steps in the manufacture of the chemical bearing pellet of FIG. 1.

DETAILED DESCRIPTION

As illustrated in FIG. 1, a pellet 10 for use in agriculture or home gardening to deliver an biocide comprises a central body portion or core 12 made essentially of a water dispersible agriculturally inert and essentially nontoxic material which contains a predetermined amount of the biocide. The biocide is contained in core portion 12 in an amount effective to substantially terminate the functioning of a significant number of target agricultural pests upon dissolution of a selected number of pellets 10 in a predetermined volume of water and application of the resulting solution to soil.

Pellet 10 further comprises a protective outer coating 14 about the chemical-bearing core 12. The coating 14 is made of a second water dispersible agriculturally inert and essentially nontoxic composition which may either be the same as or different from the water-dispersible carrier composition of the core 12.

The biocide may be interspersed essentially homogeneously throughout core 12. Alternatively, the distribution of the biocide in the agriculturally inert and essentially nontoxic composition of core 12 may vary along a gradient from the center of core 32 to the periphery thereof. In that event, core 12 may take the form of a small cup or hollow receptacle, the biocide being deposited inside the cup or receptacle during manufacture.

Where the biocide is interspersed throughout the core, the chemical is more gradually released to the environment upon dispersion of the agriculturally inert and essentially nontoxic carrier composition of the core.

As further illustrated in FIG. 1, pellet 10 also comprises a layer 16 of polymeric material between core 12 and outer coating 14. Polymeric layer 16 serves to prevent or inhibit diffusion of the biocide from core 12 to coating 14.

Pellet 10 may take virtually any size or shape. Generally, for ease of production, a cylindrical shape is considered desirable. As described hereinafter with reference to FIG. 4, the cylindrical shape of core 12 is easily produced by extrusion. The size of pellet 10 and particularly of core 12 is largely arbitrary and depends in part on how much of the biocide is to be carried in each pellet. The amount of the biocide in turn depends on the particular chemical involved and on the particular end use application, for example, whether the pellet is intended for home use or agricultural use.

Coating 14 facilitates handling of the pellets 10 inasmuch as no special or extraordinary precautions need be taken. Coating 14 is nontoxic and serves as a temporary barrier to the diffusion of the biocide from core 12. This barrier function is also performed by polymeric layer 16.

In using pellets 10, a home owner, gardener, farm hand, etc., first determines the size of the area to be treated with the biocide. A number of pellets 10 is selected by the user in accordance with the size of the application. Thus, doubling the area to be protected generally requires double the number of pellets. The selected pellets are simply placed into a container of water and allowed to disperse. Upon dispersion of the pellets, the biocide becomes dissolved in the water. The residue from the agriculturally inert and essentially nontoxic compositions is partially dissolved, partially suspended in solution and may precipitate out to a minor extent. The residue, however, is essentially completely dispersible in water and does not clog spraying or other application equipment.

As depicted in FIG. 2, another pellet 20 for use in agriculture or home gardening to deliver a biocide comprises a central body portion or core 22 and a protective outer coating 24 without an intermediate polymeric layer as shown in FIG. 1. As described hereinabove, with reference to FIG. 1, core 22 comprises a water dispersible agriculturally inert and essentially nontoxic material which contains a predetermined aliquot of the biocide. The biocide is contained in core 22 in an amount effective to substantially terminate the functioning of a significant number of target agricultural pests upon dissolution of a selected number of pellets 20 in a predetermined volume of water and application of the resulting solution to soil, plants, a body of water, etc. Coating 24 is made of a second water dispersible agriculturally inert and essentially nontoxic composition which may either be the same as or different from the water-dispersible carrier composition of the core 22.

The pellet 20 of FIG. 2 may be useful in cases where the storage time of the pellets, i.e., the interval between manufacture and use, is not expected to be of especially long duration. In that case the pellets 20 can be handled safely without fear of contamination by the biocide. It is to be noted that the thickness of outer coating 24 may be varied in this case to provide a greater distance that the biocide must diffuse in order to reach the surface of the pellet 20.

Figure 3:
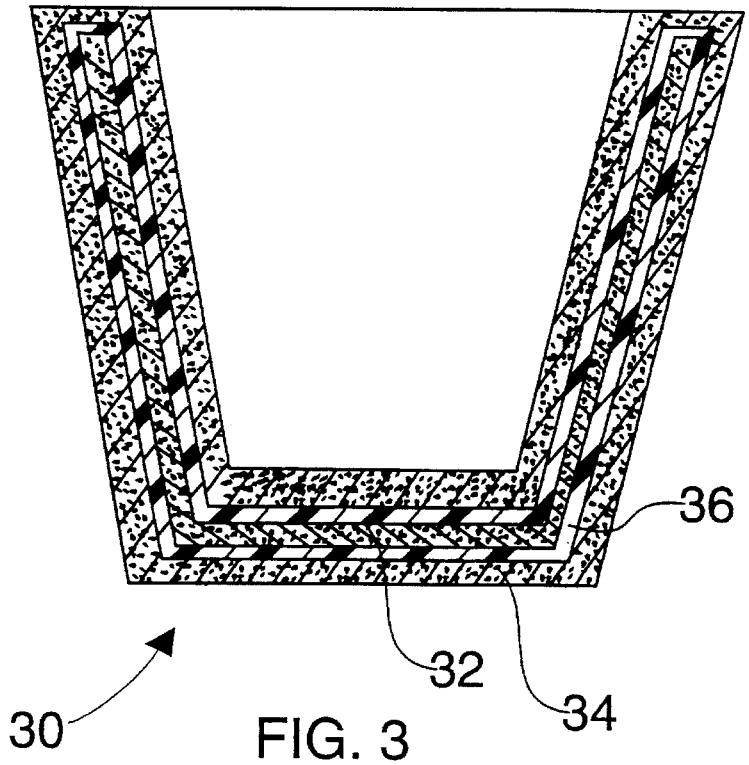

As shown in FIG. 3, a delivery system or device takes the form of a cup or pot 30 comprising a cup-shaped central body portion or core 32 and optionally, a protective outer coating 34, and an optional intermediate polymeric layer 36. In use, a seedling or young vegetable specimen may be planted in pot 30, for example at a shipping center. The seedling with pot 30 is subsequently planted in soil at a destination or ultimate use station. As the pot 30 gradually dissolves or disperses in the soil in response to rain and waterings, the biocide gradually diffuses into the soil about the roots of the seedling and serves to kill, destroy or terminate nematodes or other agricultural pests.

In certain embodiments according to the present invention, the central body portion or core 32 is made of a water dispersible composition and biocide is simply placed within the central body portion cavity 31 in combination with a filler, dispersant or other additive. The body portion is capped or has a lid 33 made of a water dispersible material which seals the biocide within the body portion cavity and prevents the biocide from escaping before delivery, for example during transport. In preferred embodiments, the body portion 32 and lid or cap 33 are made of the same water dispersible composition.

Core 32 is made essentially of a water dispersible agriculturally inert and essentially nontoxic material which contains a predetermined aliquot of the biocide. The biocide may be interspersed substantially uniformly thoughout core 32 and is including within the present invention an amount effective to substantially terminate the functioning of a significant number of target agricultural pests such as nematodes upon gradual dissolution of pot 30.

Pot 30 may further comprise a protective outer coating 34 about the chemical-bearing core 32. The coating 34 is made of a second water dispersible agriculturally inert and essentially nontoxic composition which may either be the same as or different from the water-dispersible carrier composition of the core 32.

Pot 30 may take virtually any size or shape. Core 32 is preferably produced by press molding or injection molding a dough of the respective agriculturally inert and essentially nontoxic composition containing a predetermined concentration of the biocide. However, other techniques may be used, depending, for example, on the number of pots to be produced and the sizes and shapes of the pots. A small number of symmetrical chemical-delivery pots may be produced, for instance, by throwing on a potter's wheel.

Upon formation, core 32 is dried in a convection oven and additionally or alternatively in a microwave oven. If polymeric layer 36 is to be used, to provide delayed diffusion of the biocide from core 32 to coating 34, liquified polymer is then applied to the core by spraying, rolling, dipping, or brushing. The polymeric layer 36 is dried before the application of the outer coating 34. Preferably, coating 34 is molded onto the core 32. Alternatively, core 32 (with polymeric layer 36) may be dipped into a vat of the dough for forming the outer coating 34, provided that the dough is wet enough to adhere in a layer like coating to core 32 during a dipping process. Several dippings with alternate drying steps may be undertaken to ensure a coating 34 which is sufficiently thick.

The biocide is preferably a biocide such as an insecticide, fungicide, nematocide or herbicide. More particularly, the biocide is a compound taken from the group consisting of propoxur, chlorpyrifos, diazinon, malthlon, carbaryl, fenvalerate, methomyl, acephate, permethrins, and diflubenzuron.

The following examples are provided for purposes of illustrating the present invention. These examples are presented only for illustration purposes and are not to be viewed as a limitation of the scope of the invention.

Following are several examples with parts indicated by weight of components of the water dispersible agriculturally inert and essentially nontoxic compositions which may be used in cores 12, 22, and 32 and coatings 14, 24, and 34 as well as for other uses.

EXAMPLE 1

35 parts cellulose ether 10 parts zinc stearate 10 parts cellulose tissue fiber

When combined with water to form a dough and then heated in a sheet-like form ($1/16$–$1/8$ inch) in a convection oven at approximately 200° C., this composition dries to form a web which is as as hard and tough as shoe leather and yet can disperse in water within hours or days.

EXAMPLE 2

35 parts cellulose ether 10 parts zinc stearate 10 parts unbleached cellulose fiber When combined with water to form a dough and then heated in a sheet-like form ($1/16$–$1/8$ inch) in a convection oven at approximately 200° C., this composition also dries to form a hard and tough water-dispersible material.

EXAMPLE 3

19 parts cellulose ether 6 parts zinc stearate 100 parts water-saturated cellulose tissue fiber 10 parts calcium carbonate (e.g., SUPER FLEX 200)

In this composition, the cellulose tissue fiber is water saturated in order to facilitate shredding of the tissue into small (on the order of hundredths of a square inch) segments.

EXAMPLE 4

27 parts cellulose ether 8 parts zinc stearate 100 parts water-saturated cellulose tissue fiber 10 parts calcium carbonate (e.g., SUPER FLEX 200)

10 parts polyvinylalcohol (e.g., VINOL 203)

In this composition, the cellulose tissue fiber is water saturated also in order to facilitate shredding of the tissue into small segments. It is to be noted that the agriculturally inert and essentially nontoxic composition of this example, when heated as a $1/16$ inch to $1/8$ inch slab of dough in a convectional oven at 60° C. and then subjected to microwave radiation, forms a styrofoam-like material which is flexible and yet tough so that it is not as prone to cracking as styrofoam.

EXAMPLE 5

27 parts cellulose ether 8 parts zinc stearate 100 parts cellulose tissue fiber (water-saturated, then squeezed out by hand)

This composition, when mixed with water to form a dough and then heated as a 1/16 inch to 1/8 inch slab of dough in a convectional oven at 60° C. and then subjected to microwave radiation, forms a flexible and tough material.

EXAMPLE 6

27 parts cellulose ether 8 parts zinc stearate 100 parts cellulose tissue fiber (water-saturated, then squeezed out by hand)

20 parts polyvinylalcohol (e.g., VINOL 203)

This composition, when mixed with water to form a dough and then heated as a 1/16 inch to 1/8 inch slab of dough in a convectional oven at 60° C. and then subjected to microwave radiation, also forms a flexible and tough material.

EXAMPLE 7

10 parts 110 micron length cellulose fiber (Solka-Floc™ 900)

8 parts 280 micron length cellulose fiber (Solka-Floc™ 1016)

4 parts CMC 7LXF (Low Viscosity CMC, Aqualon Corp.)

2 Parts Sodium Bicarbonate

2 Parts Citric Acid (Dry)

80 Parts Water

The final product after drying only contains about 3% of the initial water. The final product contains approximately 14.1% binder.

EXAMPLE 8

5 Parts 110 micron length cellulose fiber (Solka-Floc™ 900)

5 Parts 280 micron length cellulose fiber (Slka-Floc™ 1016)

10 Parts Softwood Pulp 2.125 Parts Hydroxypropylcellulose (Klucel™ medium viscosity type GF made by Aqualon Corp.)

85 Parts Water

This example illustrates that a number of cellulose ether binders may be used in compositions according to the present invention. It is also a formulaton which employs the dough processing technique and contains binder at a 9.6% concentration of the dry ingredients. Since the final product contains about 3% of the original water, the final product contains approximately 8.6% water.

EXAMPLE 9

6 Parts Softwood Pulp

6 Parts Hardwood Pulp

10 Parts CMC 7LXF

1000 Parts Water

This is the most basic formulation for molded pulp processing. The CMC is placed into solutin with the water (1% solution) and then the fiber is added to make a slurry. During primary molding 75%–90% of the binder solution is drawn off by vacuum, leaving 6 parts softwood fiber and 6 parts hardwood fiber+(1 to 2.5 parts CMC and 100 to 250 parts water) in the product. This yields a final binder concentration in the dried product of 7.5% to 16.7%.

EXAMPLE 10

15 Parts Softwood Pulp

15 Parts Hardwood Pulp

6 Parts CMC 7LXF

1000 Parts Water

This is another basic formulation for molded pulp processing. The CMC is placed into solution with the water (0.6% solution) and then the fiber is added to make a slurry. During primary molding 75% to 90% of the binder solution is drawn off by vacuum, leaving 15 parts CMC and 15 parts hardwood fiber=(0.6 to 1.5 parts CMC and 100 to 250 parts water) in the product. After drying the final binder concentration ranges from about 1.9% to 4.6%.

Figure 4:
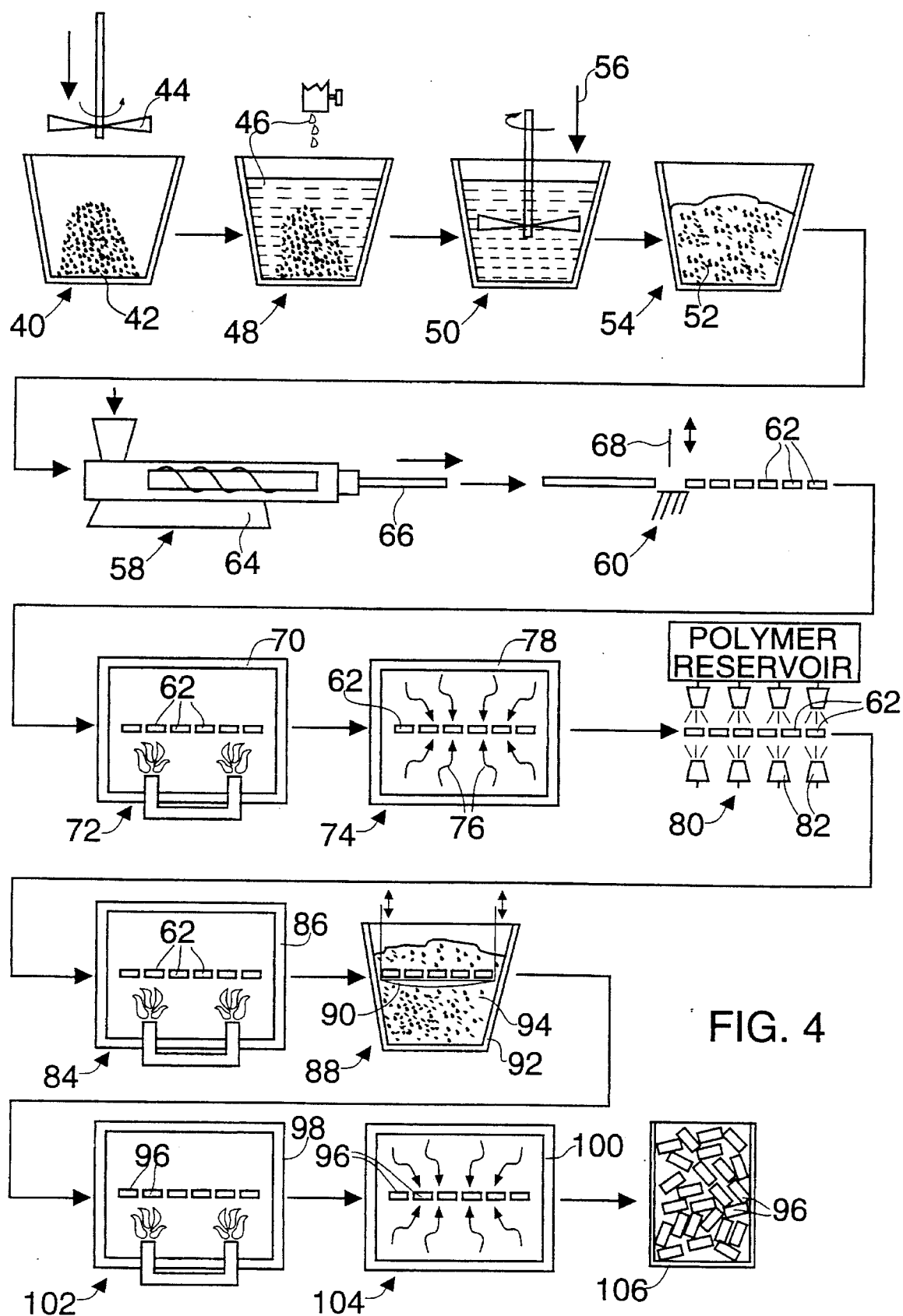

As illustrated in FIG. 4 at 40, in manufacturing a chemical delivery pellet or device from the compositions any of the above-listed examples, one generally first mixes the dry ingredients in the respective amounts to make a substantially uniform mixture 42. Mixing may be accomplished automatically, as schematically illustrated at 44. Upon formation of the uniform mixture 42, water 46 and any wetted ingredients (not shown) are then added to the dry mixture in a step 48. In a subsequent step 50, the water 46 and the wet ingredients are mixed with the dry ingredients of mixture 42 to form a dough 52 (step 54) of the desired consistency. The consistency depends in part on the technique for forming the pellet and the size of the pellet. To the dough is added the liquid biocide, as indicated at step 48 by an arrow 56.

In compositions which contain substantial quantities of cellulose fibers derived from wood pulp, the dry ingredients other than the cellulose fibers are first added to water and mixed to form a uniform mixture and thereafter the cellulose fibers are added to the mixture to produce a composition which may be forming into pellets or other structures using match molds, standard vacuum forming techniques and related molded fiber techniques readily available in the art.

To determine an appropriate amount of the biocide, one selects first a unit dose of the chemical, that is, the smallest dose which may be used in any contemplated application. This dose corresponds to one pellet. If, for example, one teaspoon of a particular biocide (e.g., from the above-listed chemicals) is added to ten gallons of water in accordance with the manufacturer's directions, but a smallest dose might be two gallons for a limited application (e.g., home use), then one teaspoon of the biocide is to be added to an amount of the core dough which will make five pellets. If the pellet size is selected to be about 28 grams, then the biocide is added to the dough in an amount so that one teaspoon of the chemical corresponds to 140 grams of the initial mixture.

The dose sizes for the different biocides, e.g., propoxur, chlorpyrifos, diazinon, malthlon, carbaryl, fenvalerate, methomyl, acephate, permethrins, and diflubenzuron, among numerous others, are available from the respective manufacturers.

Upon the formation of dough 52 containing the appropriate amount of the respective biocide, the dough is manipulated in steps 58 and 60 to form pellets 62 of the predetermined size and shape. More particularly, an extruder 64 is operated to extrude a rod 66 of a predetermined thickness. In step 60, rod 66 is cut by a reciprocating blade 68.

Pellets 62 are conveyed to a convection oven 70 for drying in a step 72. The drying temperature in convection oven 70 is in a range between approximately 50° C. and approximately 300° C. The lower end of the temperature range is selected in the event that the pellets 62 are subjected in a subsequent step 74 to microwave radiation 76 in a microwave oven 78.

It is to be noted that cutting step 60 and drying steps 72 and 74 may be reversed, in which case reciprocating cutting blade 68 is replaced by a saw blade (not shown).

After drying of pellets 62 in steps 72 and 74, a polymeric layer is applied in a step 80 via spray nozzles 82. Alternatively, the polymeric layer is applied via a rolling, brushing, or dipping operation. In a subsequent step 84, the polymeric layer is dried in an oven 86.

Figure 2:
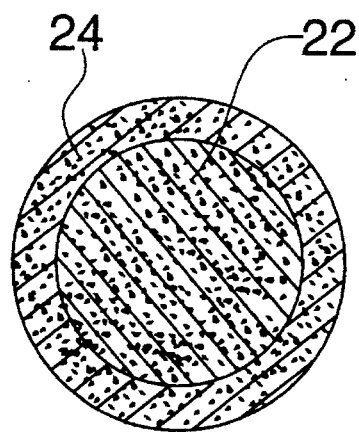

As discussed above with reference to FIG. 2, the polymeric layer may be omitted. In that case, pellets 62 are conveyed from ovens 70 and 78 directly to a dipping step or station 88.

In dipping step 88, dried pellets 62 are lowered via an elevator device 90 into a vat 92 containing a dough 94 made from a water dispersible agriculturally inert and essentially nontoxic composition such as one of the compositions listed in the examples above. Dough 94 is substantially more fluid than dough 52, whereby the dough coats about pellets 62 to form new pellets 96.

Coated pellets 96 are dried in a convection oven 98 and, optionally, a microwave oven 100 in a pair of consecutive steps 102 and 104. Steps 88, 102 and 104 may be performed several times to provide pellets 96 with coatings of a predetermined desired thickness. As discussed hereinabove, the thickness of the protective coatings on the pellets 96 may be increased (particularly in the case of the pellet 20 shown in FIG. 2) to augment the barrier function of the coating.

Protective coatings 14 and 24 may be provided on cores 12 and 22 in ways other than that shown in steps 88, 102 and 104 of FIG. 4. For example, coatings 14 and 24 may be formed by rolling the cores in the coating dough or, particularly in the case of large pellets, molding the coating dough about the cores.

A load of pellets 96 may be shipped in a container 106. No special or extraordinary precautions need be taken for the disposition of container 106 after use of pellets 96 contained therein. The pellets 10, 20, 96 themselves may be handled by hand without danger of contamination by the biocide.

From the above examples, it is seen that the various components of the agriculturally inert and essentially nontoxic compositions have weight percentage ranges as follows. The cellulose fiber, whether in the form of shredded tissue paper, unbleached cellulose fiber or wood pulp, preferably comprises about 10% to about 95%, more preferably about 20% to about 75% by weight of the respective water dispersible agriculturally inert and essentially nontoxic composition, whether used in the core 12 (FIG. 1), 22 (FIG. 2) or 32 (FIG. 3) of the chemical delivery pellet or article or in the protective outer coating 14, 24 or 34 or in other applications. The water soluble cellulose ether preferably comprises between approximately 2% and 75%, preferably about 10% to about 65%, by weight of the composition.

In addition, a gas releasing agent may also be included in compositions according to the present invention generally in an amount ranging from about 0% to about 30% by weight and preferably about 0% to about 15% by weight of the composition. A biologically compatible, biodegradable organic acid, for example, citric acid, among numerous others, is also preferably included in certain compositions according to the present invention. The acid and gas releasing agents are combined preferably in molar ratios ranging from about 1:10 to about 10:1 (acid to gas releasing agent) and most preferably in about a 1:1 molar ratio.

Other additives may also be included. For example, where a salt of stearate is used, the stearate salt preferably comprises about 4% to about 25% by weight of the composition.

Calcium carbonate preferably comprises between approximately 0% and 10% of the respective water dispersible agriculturally inert and essentially nontoxic composition, while polyvinylalcohol preferably comprises between approximately 0% and 15% of the respective water dispersible agriculturally inert and essentially nontoxic composition. Other additives such as surfactants, coloring agents, other inert fillers, binders and other additives also may be included in compositions according to the present invention.

In the manufacturing method illustrated in FIG. 4, if rod 66 takes the form of a tube, a core may be formed inside the tube upon the drying thereof, the core being a water-dispersible agriculturally inert and essentially nontoxic composition of one of the above examples containing a predetermined amount of the selected biocide. The core may be formed by injecting or otherwise depositing a dough made of the selected agriculturally inert and essentially nontoxic composition and containing the selected biocide. The core is dried and the tube with the core is cut to form a plurality of segments. Alternatively, the tube may be cut prior to the deposition or insertion of the chemical-bearing dough. The ends of the segments are capped with another dough including water and a water dispersible agriculturally inert and essentially nontoxic composition. Subsequently, the capped ends of the segments are dried.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A delivery system for a biocide comprising:

a body portion including a first water dispersible agriculturally inert and essentially nontoxic composition and an amount of the biocide effective to substantially terminate the functioning of a significant number of target agricultural pests upon application of said biocide to a substrate via the delivery system, said body portion having a predetermined size and a predetermined shape; and a protective coating, about said body portion, of a second water dispersible agriculturally inert and essentially nontoxic composition, whereas at least one of said first or second water dispersible composition includes a water dispersible cellulose ether and cellulose fiber.

2. The delivery system defined in claim 1 wherein said body portion takes the shape of a pellet.

3. The delivery system defined in claim 1 wherein said body portion takes the form of a container.

4. The delivery system defined in claim 3 wherein said container is cup-shaped.

5. The delivery system defined in claim 1 wherein said biocide is interspersed throughout said first water dispersible composition.

6. The delivery system defined in claim 1 wherein said body portion is hollow and defines a chamber, said biocide being disposed at least partially within said chamber.

7. The delivery system defined in claim 1 wherein said biocide is taken from the group consisting of dimethoate, vydate, vendex, metasystox-R, fluvalinate and kethane, invermectin, propoxur, chlorpyrifos, diazinon, malathion, carbaryl, fenvalerate, methomyl, acephate, permethrins, and diflubenzuron.

8. The delivery system defined in claim 1 wherein said cellulose fiber comprises between about 10% to about 95% by weight of said first or said second water dispersible composition.

9. The delivery system defined in claim 1 wherein said cellulose ether comprises about 2% to about 75% by weight of said first or said second water dispersible composition.

10. The delivery system defined in claim 1 wherein said first or said second water dispersible composition further includes a salt of stearic acid in an amount ranging from about 4% to about 25% weight of said water dispersible composition.

11. The delivery system defined in claim 1 wherein said cellulose fiber is shredded tissue paper.

12. The delivery system defined in claim 1 wherein said cellulose fiber is unbleached cellulose fiber.

13. The delivery system defined in claim 1 wherein said first or said second water dispersible composition further includes a gas releasing agent.

14. The delivery system defined in claim 13 wherein said gas releasing agent ranges from about 0% to about 30% by weight of said first or said second water dispersible composition.

15. The delivery system defined in claim 1 wherein said gas releasing agent is a salt of biocarbonate.

16. The delivery system defined in claim 15 further including a biodegradable, biologically compatible organic acid.

17. The delivery system defined in claim 1 wherein said second water dispersible composition is different from said first water dispersible composition.

18. The delivery system defined in claim 1 wherein said second water dispersible composition is substantially the same as said first water dispersible composition.

19. The delivery system defined in claim 1 wherein said first water dispersible composition further includes a surfactant.

20. The delivery system defined in claim 1, further comprising a layer of a water soluble polymer between said body portion and said coating.

21. The delivery system defined in claim 20 wherein said polymer is taken from the group comprising acrylics, polyvinylidene chloride, ionomers, polyvinylalcohol, and polyethylhydroxycellulose.

* * * * *